US006847840B2

(12) United States Patent
DePasquale et al.

(10) Patent No.: US 6,847,840 B2
(45) Date of Patent: Jan. 25, 2005

(54) SYSTEM AND METHOD FOR STATISTICAL ANALYSIS OF QT INTERVAL AS A FUNCTION OF CHANGES IN RR INTERVAL

(75) Inventors: Michael J. DePasquale, Pawcatuck, CT (US); Anthony A. Fossa, Mystic, CT (US); David L. Raunig, New London, CT (US)

(73) Assignee: Pfizer, Inc., Groton, CT (US)

(*) Notice: Subject to any disclaimer, the term of this patent is extended or adjusted under 35 U.S.C. 154(b) by 489 days.

(21) Appl. No.: 09/960,546

(22) Filed: Sep. 21, 2001

(65) Prior Publication Data

US 2002/0062088 A1 May 23, 2002

Related U.S. Application Data

(60) Provisional application No. 60/234,912, filed on Sep. 25, 2000.

(51) Int. Cl.[7] .................................................. A61B 5/04
(52) U.S. Cl. ....................................... 600/516; 600/509
(58) Field of Search ................................ 600/509, 516

(56) References Cited

U.S. PATENT DOCUMENTS 5,306,293 A * 4/1994 Zacouto ........................ 607/17
6,238,350 B1 * 5/2001 Neilson ...................... 600/508

OTHER PUBLICATIONS

D. Raunig, et al. *Statistical analysis of QT interval as a function of changes in RR interval in the conscious dog*, Journal of Pharmacological and Toxicological Methods 46 (2001) 1–11.

* cited by examiner

*Primary Examiner*—Mark Bockelman
(74) *Attorney, Agent, or Firm*—Peter C. Richardson; Charles Ashbrook; John H. Engelmann

(57) ABSTRACT

A system and method for statistically analyzing QT interval as a function of changes in the RR interval. The system and method utilize three statistical comparisons to fully characterize the QT response: (1) the comparison of curves to give an overall effect; (2) the incidence of points exceeding a baseline upper 95% single-point prediction bound to reflect the degree of heterogeneity of ventricular repolarization; and (3) the magnitude of these points to provide a quantitative assessment of treatment-induced changes in the QT-RR relationship. The system and method use the relationship between the QT interval and heart rate (RR interval) to reference a control baseline response. Data from mammals such as humans and dogs, and pharmacological maneuvers using both cardiac and non-cardiac therapeutic agents, may be used with this multi-parameter statistical system and method. Additionally, the system and method quantifies the incidence and magnitude of points lying outside the upper 95% single-point prediction limit of the regression analysis for vehicle versus treatment.

15 Claims, 8 Drawing Sheets

SYSTEM AND METHOD FOR STATISTICAL ANALYSIS OF QT INTERVAL AS A FUNCTION OF CHANGES IN RR INTERVAL

CROSS-REFERENCE TO RELATED APPLICATIONS

The present application is a U.S. non-provisional application. This application claims the benefit of U.S. application Ser. No. 60/234,912, filed on Sep. 25, 2000 under 35 USC 119(e).

FIELD OF THE INVENTION

The present invention relates generally to QT intervals, and, more particularly to a system and method of statistical analysis of QT interval as a function of changes in ventricular heart rate.

DESCRIPTION OF THE RELATED ART

The duration of cardiac ventricular depolarization and repolarization is represented as the QT interval, which extends from the beginning of the QRS complex to the end of the T wave on an electrocardiogram (ECG), see FIG. 1. QT interval prolongation has been associated with the occurrence of arrhythmias, including torsade de pointes, a polymorphic ventricular tachycardia, which can lead to sudden death. Cardiovascular agents such as sotalol, as well as non-cardiovascular therapeutic agents terfenadine (Seldane®) and cisapride (Propulsid®) have caused QT prolongation and sudden death in humans. This has resulted in a more aggressive review by regulatory agencies of data supporting new drug applications. Therefore, a rigorous assessment of pre-clinical and clinical studies evaluating QT interval is advocated for both cardiac and non-cardiac therapeutic agents in development.

Changes in heart rate play a major, though not exclusive, role in QT interval variation. Other sources of variation in QT interval include measurement technique, sympathetic and parasympathetic activity, electrolyte disorders ($K^+$, $Ca^{2+}$, $Mg^{2+}$), changes in cardiac afterload, diseases states, and drug modulators of channel activity within the myocardium. The QT interval, though, typically increases with decreasing heart rate ("HR"), reflected by an increase in the interval between heartbeats, or RR interval of the electrocardiogram, as shown in FIG. 1.

Considerable debate has centered on how to compensate QT for changes in heart rate to provide a corrected QT interval (QTc). The most common approaches use Bazeft or Fridericia's correction, which divide QT by the square root or cube root of the preceding RR interval, respectively. This calculation normalizes the QT interval to a heart rate of 60 beats/min (RR interval of 1 second) and provides the analyst with a single metric from which to assess changes in the QT trend. Both methods have their limitations when trying to compare subjects that have different heart rates. These one-parameter models under-correct QT at high heart rates and over-correct QT at heart rates below 60 beats/min. Undercorrection can lead to a false positive indication of problems while overcorrection may mask the potential hazards of high QT intervals. There is a growing consensus among experts that QT should not be corrected for heart rate. Instead, one should report and compare the QT interval at equivalent heart rates (for example, $QT_{50}$, $QT_{60}$, $QT_{100}$ for heart rates of 50, 60, and 100 beats/min, respectively). This approach for interpreting variation in QT is not dependent solely on heart rate but the chosen heart rates are ad hoc.

For a wide range of human subjects, the RR intervals for individual cardiac cycles vary enough to establish a functional relationship between QT and RR. Pre-clinically, in vivo animal models such as the dog have been used to measure QT versus RR interval relationships. A multi-parameter regression analysis can be used to relate QT as a function of the previous RR interval for a single subject or a group of subjects.

While curve-fitting can characterize the average trend of the QT-RR relationship, heart rate corrections for QT do not account for an increase in QT variance as a function of RR. Increased variability in the QT intervals result in episodes of prolonged QT that are significantly higher than normal. Depending on the nature of these prolonged episodes, they may not be detected by any change in the curve that is determined by the majority of the other non-prolonged points.

SUMMARY OF THE INVENTION

The present invention satisfies the need to analyze the RR-compensated QT trend as well as any significant increase in QT variance. The present inventors have found that three statistical comparisons are required to fully characterize the QT response to pharmacological intervention: (1) a comparison of post compound dose and pre compound dose curves to give an overall effect; (2) the incidence of points exceeding, for example, an upper 95% confidence bound of the pre-dose curve to reflect the degree of heterogeneity of ventricular repolarization; and (3) the magnitude of these points to provide a quantitative assessment of compound induced changes in the QT-RR relationship. The statistical analysis method of the present invention does not interpret variations of QT as exclusively dependent on changes in heart rate (RR interval), but rather uses the relationship to reference a control baseline response. Furthermore, this method does not exclude its utility for examining changes in QT due to disease states, electrolyte disorders, or changes in sympathetic or parasympathetic activity. Also, this method of analysis can be used to compare any two QT-RR data sets including but not limited to the following: control to treated data, baseline to diseased state, and pre-treated to post-treated timed data. Data discussed below from conscious mongrel dogs under resting conditions, and pharmacological maneuvers using both cardiac and non-cardiac therapeutic agents, support the use of the above-mentioned three statistical comparisons to fully characterize QT prolongation. The data discussed below are purely exemplary, as the present invention is not limited to use with dogs. Rather the present invention may be used equally well with humans as well as other mammals.

Additional advantages of the invention will be set forth in part in the description that follows, and in part will be learned from the description, or may be learned by practice of the invention. The advantages of the invention will be realized and attained by means of the elements and combinations particularly pointed out in the appended claims.

Further in accordance with the purpose, the present invention includes a computer readable medium that stores instructions executable by one or more processors to perform statistical analysis of QT interval as a function of changes in the RR interval compared to a control reference, including: instructions for comparing a pre-dose curve of QT interval versus RR interval to a post-dose curve of QT interval versus RR interval; instructions for determining the incidence of points of the post-dose curve that exceed an upper confidence limit of the pre-dose curve to determine the degree of heterogeneity of ventricular repolarization; and instructions for comparing the points of the post-dose curve that exceed the upper confidence limit to the pre-dose curve to determine the magnitude of these points and provide a quantitative assessment of compound induced or other changes in the QT-RR relationship.

Still further in accordance with the purpose, the present invention includes a system for statistical analysis of QT interval as a function of changes in the RR interval compared to a control reference, the system including: a memory configured to store instructions; and a processor configured to execute instructions for: comparing a pre-dose curve of QT interval versus RR interval to a post-dose curve of QT interval versus RR interval, determining the incidence of points of the post-dose curve that exceed an upper confidence limit to determine the degree of heterogeneity of ventricular repolarization, and comparing the points of the post-dose curve that exceed the upper confidence limit to the pre-dose curve to determine the magnitude of these points and provide a quantitative assessment of compound induced or other changes in the QT-RR relationship.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention. In the drawings.

DETAILED DESCRIPTION

Reference will now be made in detail to the present preferred embodiment of the invention, an example of which is illustrated in the accompanying drawings. Wherever possible, the same reference numbers will be used throughout the drawings to refer to the same or like parts.

I. Recording of Electrocardiogram

Figure 6:
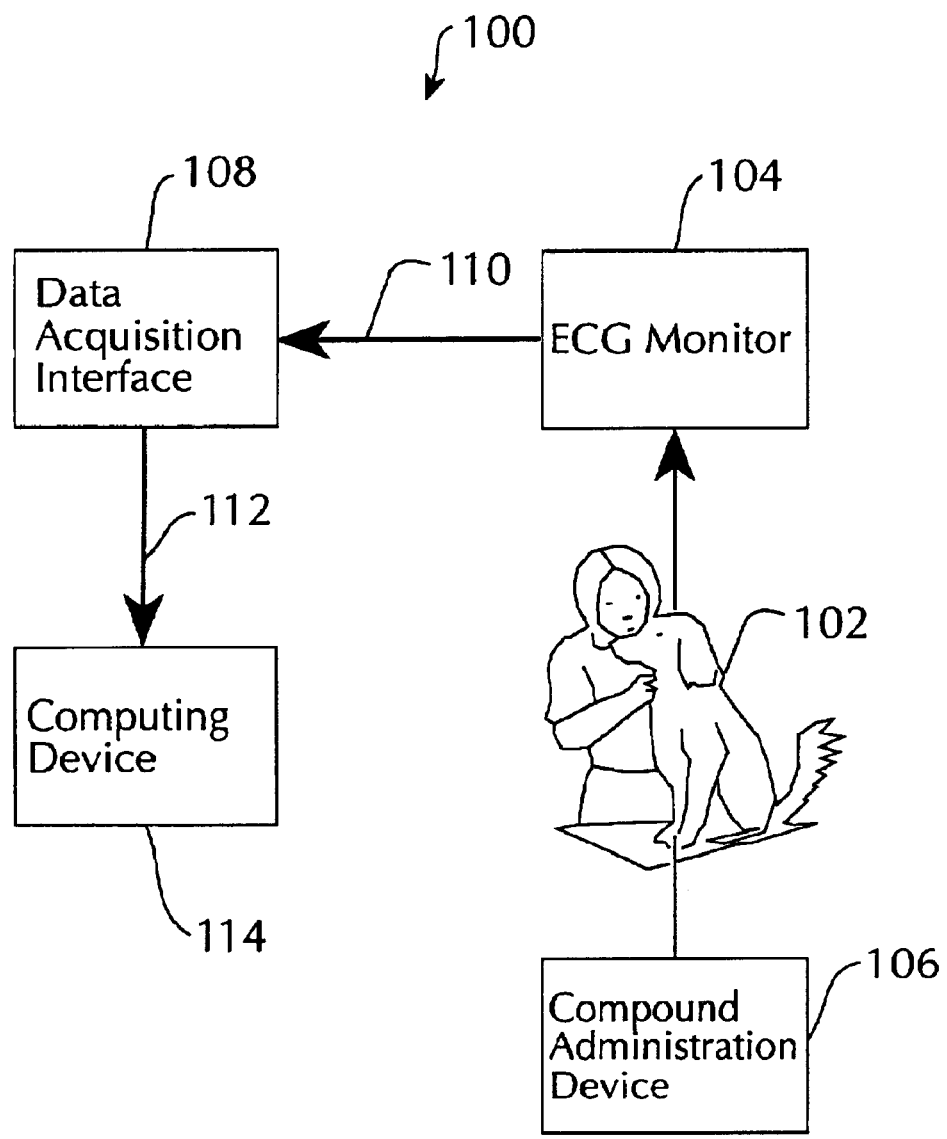
FIG. 6 is a schematic diagram showing the system for recording electrocardiogram data of the present invention.

A system for recording electrocardiogram data in accordance with the present invention is broadly shown in FIG. 6 as reference numeral 100. An electrocardiogram (ECG) monitor 104 is connected to a patient, such as a dog 102. Preferably ECG monitor 104 uses electrodes in the Lead II position, however, a QT measurement can be calculated from other ECG vectors, including Leads I and III, a VL, a VR, a VF, and all pre-cordial leads (V1–V6). A vehicle or test compound is administered to dog 102 with a compound administration device 106. The vehicle or test compound may be administered in various ways, including but not limited to orally, intravenously, or subcutaneous.

ECG monitor 104 provides signals 110 to a data acquisition interface 108 which processes the signals 110 and provides processed signals 112 to a computing device 114. Heart rate (RR interval) and Lead II ECG data are collected continuously on a beat-to-beat basis at a sampling rate of 1000 Hz to allow for millisecond (ms) resolution. Using the sampled data, the QT interval and preceding RR interval are measured on individual cardiac cycles using commercially available data acquisition and analysis software. The software package used in support of the data presented here was from Gould Inc. (Po-Ne-Mah) subsidiary. This software permits visual validation of the determination of end points used in the calculation of the ECG time intervals. The collection of data is not limited to any particular method. For example, ECG time intervals can be measured using a ECG strip chart recorder. Thus, both manual and electrical data collection is possible with the present invention.

Figure 7:
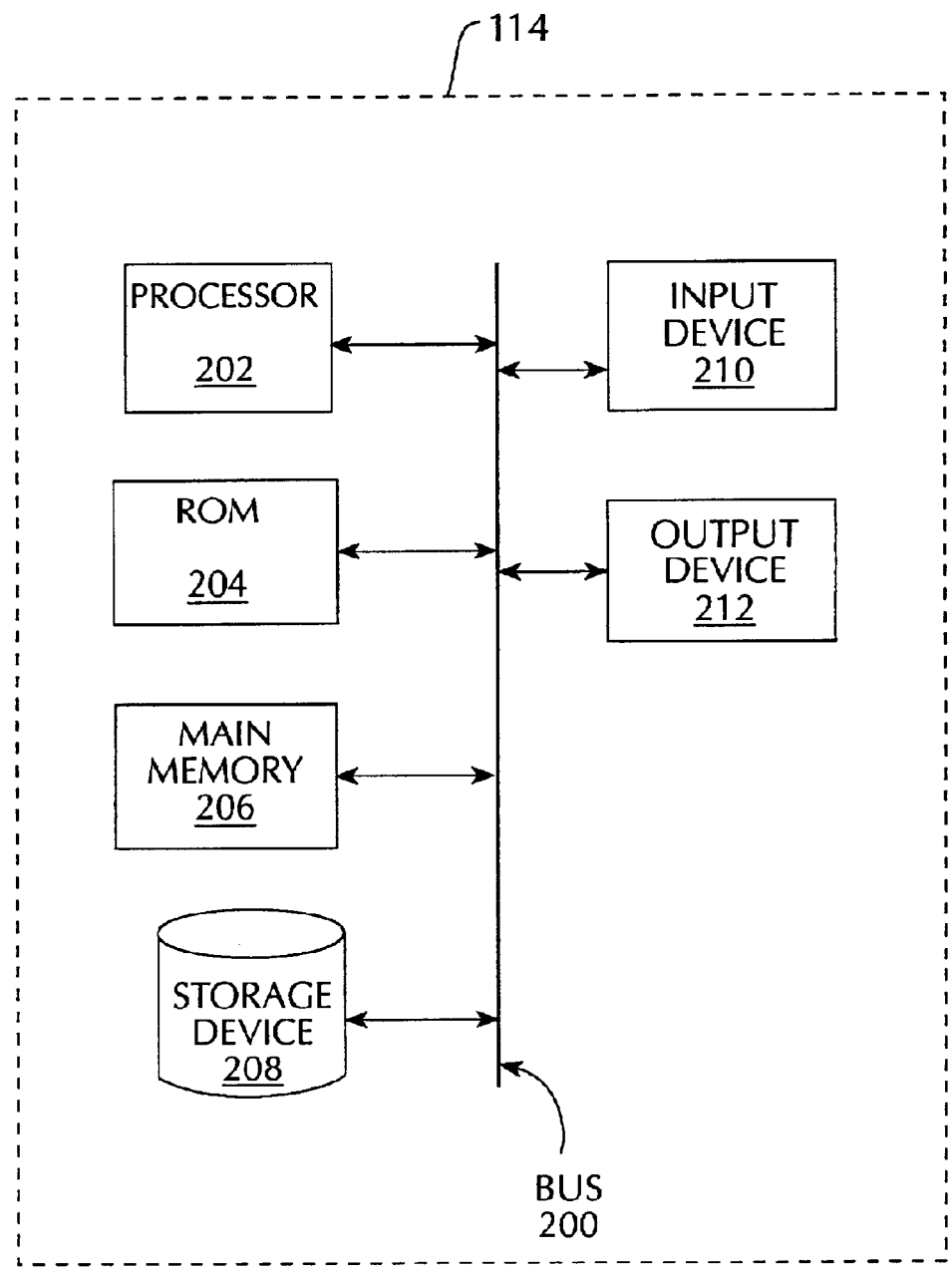
FIG. 7 is a schematic diagram showing a computing device used in the system of FIG. 6.

Computing device 114, as shown in FIG. 7, includes a bus 200 interconnecting a processor 202, a read-only memory (ROM) 204, a main memory 206, a storage device 208, an input device 210, and an output device 212. Bus 200 is a network topology or circuit arrangement in which all devices are attached to a line directly and all signals pass through each of the devices. Each device has a unique identity and can recognize those signals intended for it. Processor 202 includes the logic circuitry that responds to and processes the basic instructions that drive device 114. ROM 204 includes a static memory that stores instructions and data used by processor 202

Computer storage is the holding of data in an electromagnetic form for access by a computer processor. Main memory 206, which may be a RAM or another type of dynamic memory, makes up the primary storage of device 114. Secondary storage of device 114 may comprise storage device 208, such as hard disks, tapes, diskettes, Zip drives, RAID systems, holographic storage, optical storage, CD-ROMs, magnetic tapes, and other external devices and their corresponding drives.

Input device 210 may include a keyboard, mouse, pointing device, sound device (e.g. a microphone, etc.), biometric device, or any other device providing input to device 114. Output device 212 may comprise a display, a printer, a sound device (e.g. a speaker, etc.), or other device providing output for device 114.

As will be described below, a computing device 114 consistent with the present invention may perform a method for statistical analysis of QT interval as a function of changes in the RR interval. Device 114 performs this task in response to processor 202 executing sequences of instructions contained in a computer-readable medium, such as main memory 206. A computer-readable medium may include one or more memory devices and/or carrier waves.

Execution of the sequences of instructions contained in main memory 206 causes processor 202 to perform processes that will be described later. Alternatively, hardwired circuitry may be used in place of or in combination with software and any such arrangement wherein the device is set to perform the tasks of the algorithms disclosed herein, either by hardwire circuitry, stored instructions, or combination thereof, would comprise a means for comparing a pre-dose curve of QT interval versus RR interval to a post-dose curve of QT interval versus RR interval, determining the incidence of points of the post-dose data that exceed an upper 95% single-point prediction limit to determine the degree of heterogeneity of ventricular repolarization and a means for comparing the points of the post data that exceed the upper 95% single-point prediction limit of the pre-dose curve to determine the magnitude of these points and provide a quantitative assessment of treatment-induced changes in the QT-RR relationship instructions to implement processes consistent with the present invention. Thus, the present invention is not limited to any specific combination of hardware circuitry and software.

The various treatments with vehicle or compounds are studied in a randomized fashion. The drugs include Methanesulfonamide, N-[4-[[1-[2(6-methyl-2-pyridinyl)ethyl]-4-piperidinyl]carbonyl]phenyl] (i.e., E-4031), terfenadine, and cisapride. E-4031, an antiarrhythmic, terfenadine (Seldane®), an antihistamine, and cisapride (Propulsid®), a gastrointestinal prokinetic agent, clinically have all been shown to cause a clear, dose-dependent increase in $QT_C$. The term "vehicle" as used herein is defined as a non-reactive solvent used in the administration of the compound.

II. Analysis of QT Interval as a Function of the Preceding RR Interval

Figure 8:
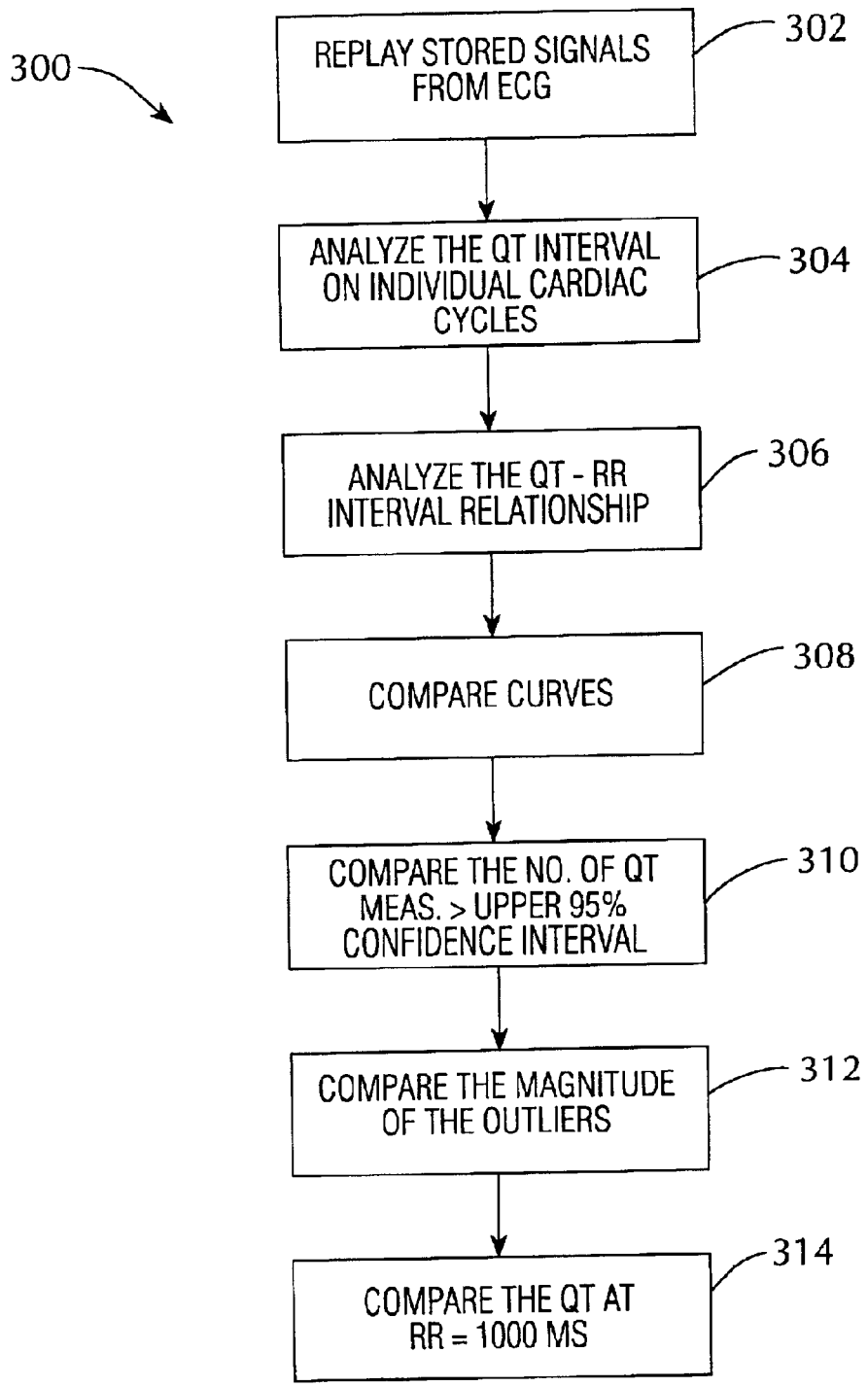
FIG. 8 is a flow chart of processing performed by the computing device shown in FIG. 7.

The method for statistical analysis of QT interval as a function of changes in the RR interval in accordance with the present invention is performed by computing device 114. As shown in FIG. 8, the method 300 of the present invention includes a plurality of steps, including the step 302 of replaying the stored data from ECG. The method further includes: a step 304 of analyzing the QT interval on individual cardiac cycles; a step 306 of statistically analyzing the QT-RR interval relationship; a step 308 of statistically comparing best fit curves of the QT-RR relationship; a step 310 of statistically comparing the number of QT interval measurements exceeding the upper 95% confidence interval; a step 312 of statistically comparing the magnitude of the outliers; and a step 314 of statistically comparing the QT at an RR interval of 1000 ms. Each of the steps of the method 300 of the present invention is explained in the following sections in greater detail.

QT Analysis on Individual Cardiac Cycles

The calibrated analog signal is replayed on computer device 114 in order to analyze QT interval measurements for individual cardiac cycles. Approximately 250 to 300 consecutive cardiac cycles are analyzed for a pre-dose period and during steady-state compound exposure. This encompasses between three to five minutes of continuous data for each data collection period. A previous analysis for statistical power for the variance of the data for the dog showed that approximately 250 points were required for a probability of 0.15 of a false negative, β, (i.e. determining the treatments to be the same when they are, in fact, different) with a Type I error rate (false positive) of α=0.05. The (α and β values were chosen from historical precedence with physiological data. Sample size determinations should be done for each type of experiment and subject. Each QT measurement is monitored by a technician on a data replay screen (e.g., a computer monitor) connected to computing device 114. If there is a discrepancy between the software analysis and the technician's interpretation of the end of the T wave, the cardiac cycle is reanalyzed interactively by the technician using on-screen measurement cursors. QT is then analyzed as a function of the previous RR interval for each cardiac cycle of a selected time period. An asymptotic decaying exponential growth curve fit is used to describe the relationship between QT and RR interval:

$$QT = A - B^* \exp(-C^* RR/1000) \quad (1)$$

The coefficients A, B, and C represent different aspects of the QT-RR relationship. The terms A, B, and C are regression coefficients that are determined by a non-linear regression technique applied to the data. The coefficients A, B, and C are unique for a given data set. The coefficient "A" represents the behavior of QT at very large values of RR. The coefficient "B" represents the behavior of QT at very low values of RR. The coefficient "C" represents the relationship of the intermediate points and the steepness of the curve between low and high RR values.

Calculation of the relationship between QT and RR interval is not limited to Equation (1). Rather, other curve fit equations may be used, including a log growth function, Bazett or Fridericia's correction (described above), and all of the equations set forth in T. Matsunaga et al., "QT Corrected For Heart Rate and Relation Between QT and RR Intervals in Beagle Dogs", Journal of Pharmacological and Toxicological Methods, 38, pp. 201–209 (1998). Another curve fit equation developed by the present inventors is an arc tan function $QT = A + B \times \arctan(C \times RR)$.

Statistical Analysis of the QT-RR Interval Relationship

All statistical comparisons used the following statistical hypotheses:

$H_0$ (null hypotheses): $\mu(\text{dose}) \leq \mu(\text{pre-dose})$ $H_1$ (alternative hypotheses): $\mu(\text{dose}) > \mu(\text{pre-dose})$ In the interest of QT prolongation, the concern is for QT values elevated above the pre-dose value for the corresponding RR interval defined by the regression analysis-fitted curve. The null hypothesis $H_0$ is a one-sided hypothesis and all rejections of the null hypothesis are based on whether the dose measurements were greater than 95% of the pre-dose data (i.e. 0.05 significance level). For treatments where the interest lies in detection of increasing QT, the one-sided hypothesis $H_0$ is the appropriate test. In this case, a QT value that is higher than 95% of the pre-dose data is determined to be different, or prolonged, from the pre-dose data, and the hypothesis $H_0$ is rejected in favor of the alternative hypothesis $H_1$. A false negative is defined as accepting hypothesis $H_0$ when it should have been rejected.

The analysis of the vehicle or compound versus pre-dose effect on QT was accomplished by a statistically significant indication of QT prolongation by at least one of the following: (1) a significant rise in QT post-dose curve above the pre-dose curve; (2) a significant increase in the number of episodes of QT intervals that exceed the pre-dose 95% prediction interval threshold; or (3) a significant increase in the magnitude by which the prolonged points exceed the pre-dose curve.

Statistical Comparison of the Curves

Equation (1) is used to fit the QT measurements to the preceding RR interval for each separate data set of consecutive cardiac cycles. The data from each sample period for each vehicle or compound dose is fit to the equation using a least squares nonlinear regression method such as, but not limited to, Quasi Gauss-Newton.

Post-dose curves are inspected to determine if and at what point the dose curve becomes significantly higher than the pre-dose curve. The upper 95% confidence limit for the difference of the curves is determined for each of the dose-to-pre-dose comparisons. If the dose curve crosses the 95% limit, the QT and RR values and the direction of crossing is noted. If the treatment curve is significantly elevated or depressed for the entire RR range, then the curves will not cross, indicative of an overall significant rise in QT or no significant overall rise, respectively.

Statistical Comparison of the Number of QT Measurements Exceeding the Upper 95% Confidence Interval The analysis of the compound versus vehicle effect on QT is also accomplished by comparisons of the number of prolonged points exceeding the 95% confidence interval of their respective pre-dose curves. The pre-dose curve value represents the least squares estimate of QT at that value of RR. The 95% limits are then used to compare the overall effect of the treatment (compound or vehicle) to that of the pre-dose response. The confidence limits of the two curves are combined (pooled) to determine the standard error of the difference between the pre-dose and post-dose curves. The single-point prediction limits for the pre-dose data are used to determine whether a QT point is significantly prolonged. The extent of the confidence and prediction limits depends on the overall variability of the data and the values of the coefficients.

The number of pre-dose data that exceed the upper 95% prediction limit (referred to herein as "outliers") is compared to the number of post-dose data that exceed the limit for each of the time periods. A repeated measures test for significant difference between pre-dose and post-dose outliers is conducted to evaluate an effect. In the case of small but consistent effects, the repeated measures test detects significant differences better than individual tests. Individual significance tests of the proportion of prolonged outliers, such as, but not limited to Chi-square and Fisher's Exact Test, are also conducted to determine if any one treatment is significantly higher than the pre-dose results. To minimize the chance of false negatives, β, conventionally known as "Type II errors," no multiple comparison adjustments are made for the individual tests.

Statistical Comparison of the Magnitude of the Outliers

Once the outliers are identified, they are compared to the pre-dose curve to estimate the magnitude of prolongation, $\Delta QT$, above the QT-RR curve fit to the pre-dose data. The magnitude of prolongation is referenced to the curve rather than the upper 95% confidence bound because the curve is the best estimate of the QT-RR functional relationship, regardless of the number of data points. The resulting $\Delta QT$ are then compared within treatment groups (dose to pre-dose) using a comparative statistical method such as, but not limited to, signed rank tests and t-test.

Statistical Comparison of the QT at RR 1000 ms

The nonlinear curve defined by Equation (1) is used to provide a least squares estimate of the QT interval at a physiologically relevant heart rate of 60 beats/min ($QT_{RR1000}$). A one-tailed Student's T-test is then used for comparison of post-dose versus the pre-dose response.

Statistical Analysis Across Treatments

When comparing two or more treatments given with the same dosing protocol, the responses are first compared to the pre-dose data and curve. Treatments include, but are not limited to, different dose levels, compounds and days. The resulting outlier numbers and magnitudes ($\Delta QT$) are then compared between treatments. For measurements at repeated intervals, a repeated measures test is conducted on the number and magnitude data for statistical significance. Individual tests are conducted without multiple comparison corrections to minimize the chance of false negatives.

A simultaneous overall measure of significant treatment effect over all measurement times provides increased statistical power for a consistent trend at all data collection periods. This overall measurement was done using a Mantel-Haenszel statistical analysis. The analysis can be done using conventional independent (such as a Chi-Square) or correlated (such as McNemar) statistical tests and can include a continuity correction for low frequencies or outliers. Individual measurements may also be performed to investigate each period's results. Other statistical tests may be performed using transformed outlier frequency data and standard repeated measures of variance (such as ANOVA, Linear Models) or categorical methods (such as logistic regression and generalized linear models).

III. Results of the QT Interval Analysis

The results of three tests for significance increases the sensitivity of detecting QT prolongation by testing for the incidence and magnitude of prolonged episodes. Conventional methods such as Bazett or Fridericia may not fit the data, depending on the range of RR intervals associated with each QT interval. Additionally, conventional testing does not account for the effects of increasing incidence in prolonged QT episodes nor do they test specifically for the magnitude of the determined outliers. The statistical method of the present invention evaluates individual responses to ensure sensitivity in detecting statistically significant effects in a heterogenous population that may otherwise mask changes if one evaluates only the pooled study group response.

Overall Rise in QT

Figure 1:
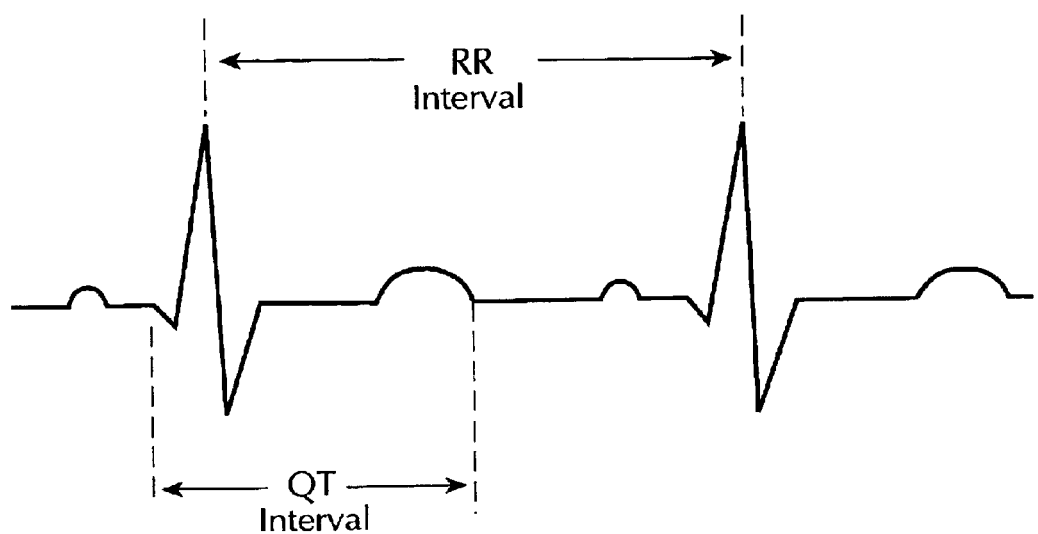
FIG. 1 is a chart showing how the QT interval is measured on an electrocardiogram.
Figure 2:
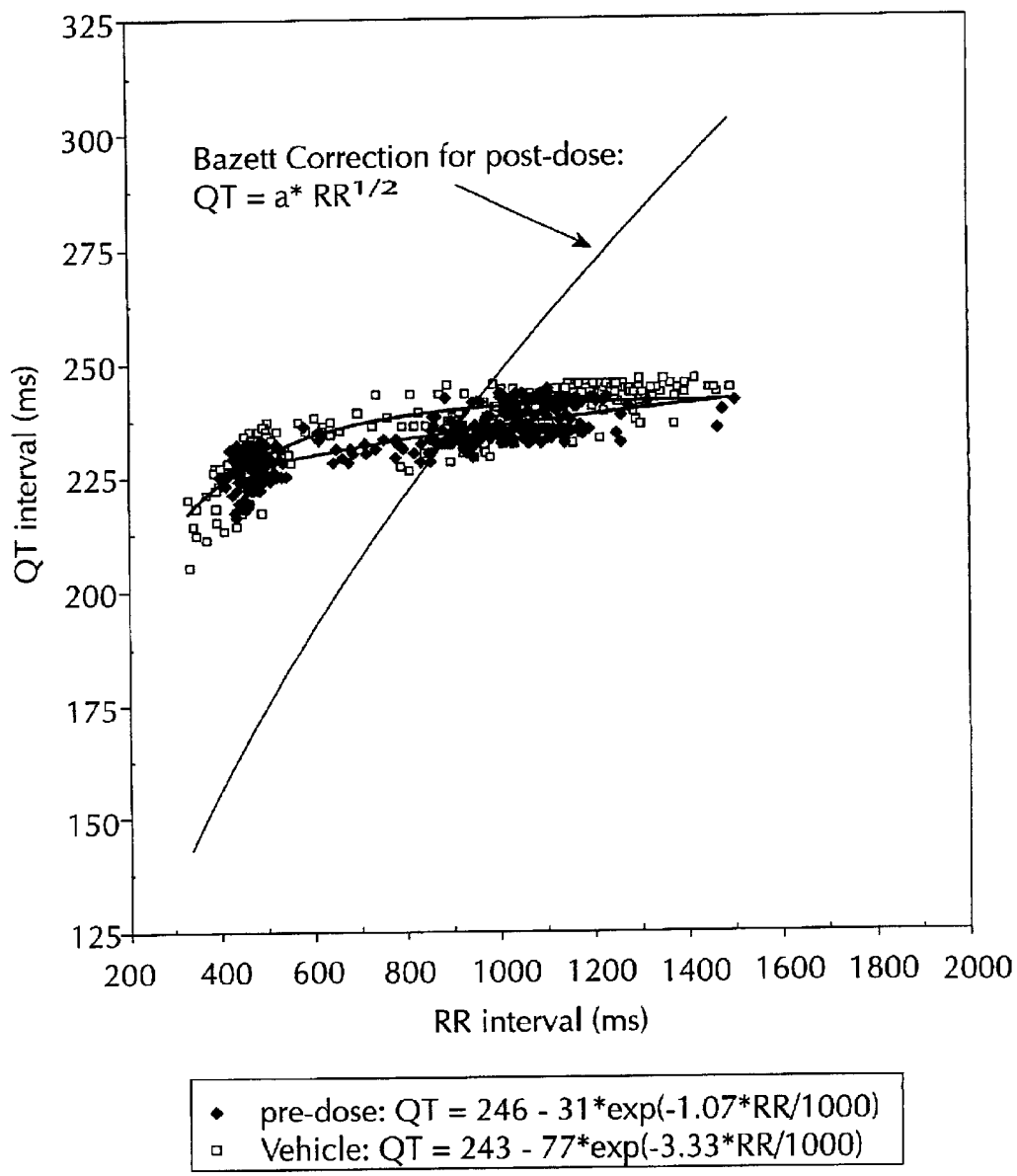
FIG. 2 is a chart showing the QT-RR interval relationship following intravenous infusion of a vehicle in the conscious mongrel dog analyzed using the system and method of the present invention.

Exemplary data of the QT-RR relationship for a variety of compounds known to prolong QT are shown in FIGS. 2–5, with the statistical analysis summarized in Table 1. The Bazett correction for the treatment curve is also included in FIGS. 2–5 to demonstrate how poorly this predicts the QT-RR relationship. The data in FIG. 2 show no difference between the vehicle and the pre-dose baseline for this dog.

Figure 3:
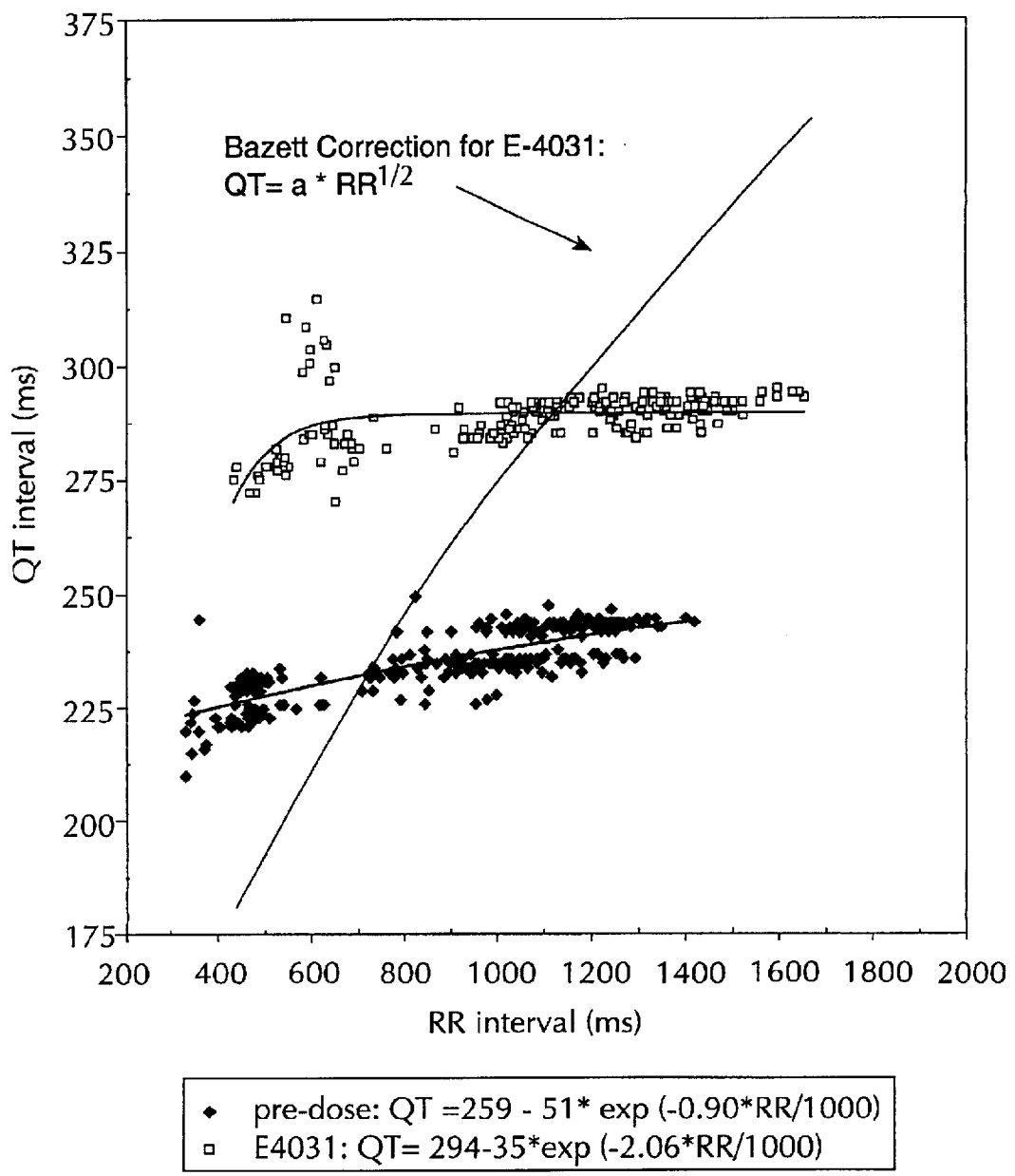
FIG. 3 is a chart showing the QT-RR interval relationship following intravenous infusion of the drug E-4031 in the conscious mongrel dog analyzed using the system and method of the present invention.
Figure 4:
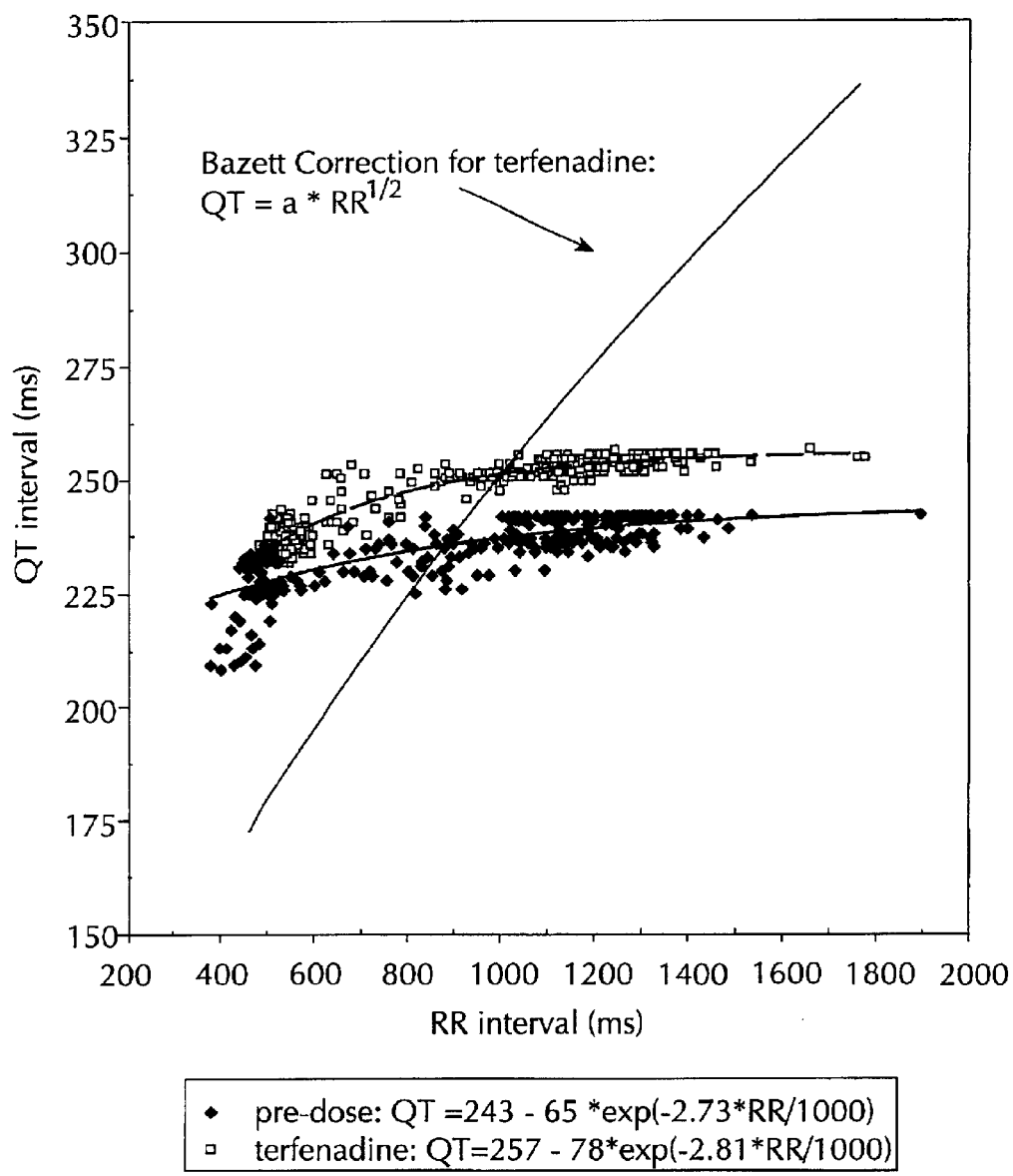
FIG. 4 is a chart showing the QT-RR interval relationship following intravenous infusion of the compound terfenadine in the conscious mongrel dog analyzed using the system and method of the present invention.
Figure 5:
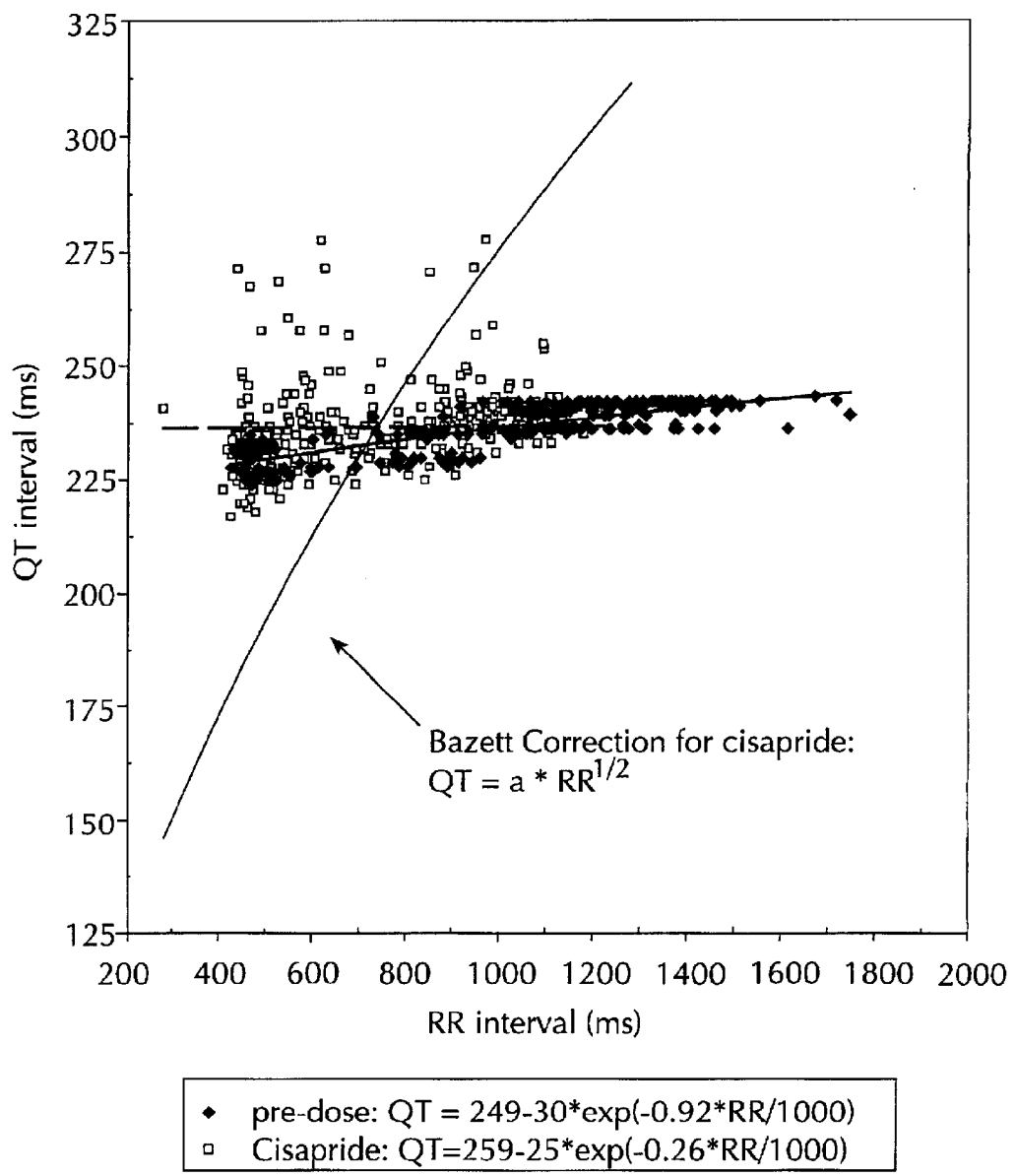
FIG. 5 is a chart showing the QT-RR interval relationship following intravenous infusion of the compound cisapride in the conscious mongrel dog analyzed using the system and method of the present invention.

For E-4031, FIG. 3 shows a large rise in overall QT over the entire RR range. The results for terfenadine, shown in FIG. 4, are slightly different from those of E-4031. The QT values of the terfenadine data are close to the baseline values for low (<600 ms) RR values. However, as with E-4031, there is a clear rise in QT values at RR values above 1000 ms. The effect of cisapride on the QT-RR relationship is shown in FIG. 5. The post-dose curve is not significantly greater than the pre-dose curve for RR>1094 ms (the crossing point of the curves). The rate dependence of the cisapride effect would not be shown in a simple measurement of QTc.

Increase in the Number and Magnitude of Prolonged QT Values

Table 1 summarizes the statistical analysis of the number and magnitude of $\Delta QT$ measurements exceeding the upper 95% confidence bounds of the curve fit. E-non-breaking E-4031, terfenadine, and cisapride all caused a significant increase in the number and magnitude of the outliers compared to the pre-dose and vehicle response.

TABLE 1

Statistical analysis of treatment effect on QT interval in the conscious mongrel dog:
Comparison of pre- versus post-dose response as well as drug versus vehicle treatment

| Treatment | Time | $^{QT}RR1000$ | #outliers/ total | Vehicle #outliers/total | Vehicle outlier Mean (range) | mean $\Delta QT$ | $\Delta QT$ range | $\Delta QT$ vs t = 0 | Vehicle vs Drug #outliers | Mean $\Delta QT$ of outliers | Treatment crosses pre-dose curve |
|---|---|---|---|---|---|---|---|---|---|---|---|
| E-4031 | Pre | 238 ± 9 | 10/313 | | | 8 | 7–23 | | | | |
|  | Post | 290 ± 12*§ | 198/198 | | | 49 | 41–87 | P < 0.001 | P < 0.001 | P < 0.001 | No |
| terfenadine | Pre | 239 ± 10 | 43/351 | Pre-dose 12/374 | Pre-dose 6 (6–8) | 9 | 8–17 | | | | |
|  | Post | 253 ± 6*§ | 271/297 | | | 14 | 8–23 | P < 0.001 | P < 0.001 | P < 0.001 | No |
| cisapride | Pre | 237 ± 6 | 14/315 | Post-dose 56/329 | Post-dose 7 (6–11) | 6 | 5–7 | | | | |
|  | Post | 240 ± 18 | 130/324 | | | 12 | 5–47 | P < 0.001 | P < 0.001 | P < 0.001 | Yes: RR = 1094 ms |

$^{QT}RR1000$ mean ± SEM was derived from the curve fit and 95% Cl.
*Denotes significant increase between pre- and post-dose measurements (P < 0.05).
§Denotes significant increase in .QT for drug response compared to .QT for vehicle treatment.

IV. Discussion of the Results

Conventional single-parameter models, such as Bazett's or Fridericia's, while able to provide one measure of prolongation, fail to adequately fit the data over the wide RR range. The single parameter model forces QT=0 at R=0. QT then increases monotonically with increasing RR, resulting in overly high QT values at RR>1000 ms. Both of these models will overestimate the QTc at low RR, calling normal values prolonged, and underestimate QTc at high RR, calling almost nothing prolonged.

The use of a multiparameter model of the present invention, rather than reporting the functional relationship of QT to RR, uses the pre-dose response over the RR domain as a baseline from which to measure the treatment response for a given experiment. Inherent differences between subject pre-treatment QT-RR relationships should be taken into account in the response of the subject to treatment. Therefore the QT response to treatment is examined within the context of the observed pre-treatment QT statistics. Effects such as change in baseline level or change in QT variability, are then accounted for and valid comparisons between subjects (or treatments) can be done.

It will be apparent to those skilled in the art that various modifications and variations can be made in the system and method of the present invention and in construction of this system and method without departing from the scope or spirit of the invention. As an example, repeated measures analysis of the number of outliers can be accomplished using transformed data or sets of 2×2 contingency tables (eg. Mantel-Haenszel).

Other embodiments of the invention will be apparent to those skilled in the art from consideration of the specification and practice of the invention disclosed herein. It is intended that the description and examples be considered as exemplary only, with a true scope and spirit of the invention being indicated by the following claims.

What is claimed is:

1. A computer-implemented method for statistical analysis of QT interval as a function of changes in the RR interval before and after administration of a dose of a compound, the method comprising the steps of:
    comparing a pre-dose curve of QT interval versus RR interval to a post-dose curve of QT interval versus RR interval;
    determining the incidence of points of the post-dose curve that exceed an upper single-point prediction limit of the pre-dose curve to determine the degree of heterogeneity of ventricular repolarization; and
    determine the magnitude that these points exceed the pre-dose QT curve and provide a quantitative assessment of treatment-induced changes in the QT-RR relationship.

2. A computer-implemented method as recited in claim 1, wherein the pre-dose curve to post-dose curve comparison step comprises the substeps of:
    using an equation to fit each QT measurement to a preceding, or set of preceding, RR intervals and provide the pre-dose curve and post-dose curves; and
    comparing the pre-dose and post-dose curves to determine if and at what point the post-dose curve becomes significantly higher than the pre-dose curve.

3. A computer-implemented method as recited in claim 1, wherein the compound is administered to a human.

4. A computer-implemented method as recited in claim 1, wherein the determining step comprises the substeps of:
    pooling the confidence limits for the pre-dose and post-dose curves to provide an estimate of the standard error of the difference between the two curves;
    using the single-point upper 95% prediction limit for the pre-dose curve to determine whether a QT point on the post-dose curve is significantly prolonged;
    conducting a repeated measures test for significance to evaluate an overall effect of the treatment over all of the time periods; and
    conducting individual significance tests of the proportion of prolonged outliers to determine if the treatment response is significantly higher than the pre-dose curve.

5. A computer-implemented method as recited in claim 1, wherein the step of comparing the points of the post-dose data that exceed the upper 95% single-point prediction limit to the pre-dose curve comprises the substeps of:
    comparing outliers to the pre-dose curve to estimate how far above the pre-dose curve they are prolonged;
    subtracting the post-dose outliers from the pre-dose curve to provide corrected .DELTA.QT values; comparing the corrected .DELTA.QT values within treatment groups, post-dose to pre-dose, and across treatments;

conducting an overall test to compare the mean .DELTA.QT of each group; and conducting a one-sided significance test on the .DELTA.QT values.

6. A computer readable medium that stores instructions executable by one or more processors to perform statistical analysis of QT interval as a function of changes in the RR interval before and after administration of a dose of a compound, the computer-readable medium comprising:

instructions for comparing a pre-dose curve of QT interval versus RR interval to a post-dose curve of QT interval versus RR interval;

instructions for determining the incidence of points of the post-dose curve that exceed an upper 95% single-point prediction limit to determine the degree of heterogeneity of ventricular repolarization; and instructions for comparing the points of the post-dose data that exceed the upper 95% single-point prediction limit to the pre-dose curve to determine the magnitude of these points and provide a quantitative assessment of treatment-induced changes in the QT-RR relationship.

7. A computer readable medium as recited in claim 6, wherein the instructions for comparing the pre-dose curve to post-dose curve comprise:

instructions for using an equation to fit each QT measurement to a preceding RR interval and provide the pre-dose curve and post-dose curves; and instructions for comparing the pre-dose and post-dose curves to determine if and at what point the post-dose curve becomes significantly higher than the pre-dose curve.

8. A computer readable medium as recited in claim 6, wherein the compound is administered to a human.

9. A computer readable medium as recited in claim 6, wherein the instructions for determining the incidence of points of the post-dose data that exceed the upper 95% single-point prediction limit comprise:

instructions for pooling the confidence limits for the pre-dose and post-dose curves to provide an estimate of the standard error of the difference between the two curves;

instructions for using the upper 95% single-point prediction limit for the pre-dose curve to determine whether a QT point on the post-dose curve is significantly prolonged;

instructions for conducting a repeated measures test for significance to evaluate an overall effect of the treatment; and instructions for conducting individual significance tests of the proportion of prolonged outliers to determine if treatment is significantly higher than the pre-dose curve.

10. A computer readable medium as recited in claim 6, wherein the instructions for comparing the points of the post-dose data that exceed the upper 95% single-point prediction limit to the pre-dose curve comprise:

instructions for comparing outliers to the pre-dose curve to estimate how far above the pre-dose curve they are prolonged;

instructions for subtracting the data of the post-dose curve from the data of the pre-dose curve to provide corrected .DELTA.QT values;

instructions for comparing the corrected .DELTA.QT values between treatments; and instructions for conducting an overall test to compare the magnitudes of each treatment .DELTA.QT.

11. A system for statistical analysis of QT interval as a function of changes in the RR interval before and after administration of a dose of a compound, the system comprising:

a means for comparing a pre-dose curve of QT interval versus RR interval to a post-dose curve of QT interval versus RR interval, determining the incidence of points of the post-dose data that exceed an upper 95% single-point prediction limit to determine the degree of heterogeneity of ventricular repolarization, and a means for comparing the points of the post-dose data that exceed the upper 95% single-point prediction limit of the pre-dose curve to determine the magnitude of these points and provide a quantitative assessment of treatment-induced changes in the QT-RR relationship.

12. A system as recited in claim 11, wherein the means for comparing the pre-dose curve to post-dose curve further:

uses an equation to fit each QT measurement data to the corresponding preceding RR interval measurement data and provide the pre-dose curve and post-dose curves; and compares the pre-dose and post-dose curves to determine if and at what point the post-dose curve becomes significantly higher than the pre-dose curve.

13. A system as recited in claim 11, wherein the compound is administered to a human.

14. A system as recited in claim 11, wherein the means for determining the incidence of points of the post-dose curve that exceed the upper 95% single-point prediction limit further:

pools the confidence limits for the pre-dose and post-dose curves to provide an estimate of the standard error of the difference between the two curves;

uses the upper 95% single-point prediction limit for the pre-dose curve to determine whether a QT point on the post-dose curve is significantly prolonged; and conducts a repeated measures test for significance to evaluate an overall effect of the compound over all of the time periods; and instructions for conducting individual significance tests of the proportion of prolonged outliers to determine if any one dose of the treatment is significantly higher than the pre-dose curve.

15. A system as recited in claim 11, wherein the means for comparing the points of the post-dose curve that exceed the upper 95% single-point prediction limit to the pre-dose curve further:

compares outliers to the pre-dose curve to estimate how far above the pre-dose curve they are prolonged;

subtracts the post-dose data from the pre-dose curve to provide corrected QT values (.DELTA.QT);

compares the corrected QT values within treatment groups, post-dose to pre-dose, and across treatment groups; and conducts an overall test to compare the magnitudes of each group.

* * * * *